United States Patent
Miksza

(12) 
(10) Patent No.: US 6,176,872 B1
(45) Date of Patent: Jan. 23, 2001

(54) RADIAL STRENGTH STENT

(75) Inventor: Anthony S. Miksza, Bethlehem, PA (US)

(73) Assignee: Ethicon, Inc., Somerville, NJ (US)

(*) Notice: Under 35 U.S.C. 154(b), the term of this patent shall be extended for 621 days.

(21) Appl. No.: 08/515,344

(22) Filed: Aug. 15, 1995

(51) Int. Cl.[7] ............................................. A61F 2/06
(52) U.S. Cl. .................................................. 623/1.15
(58) Field of Search ................................ 606/191, 194, 606/195, 198, 200; 623/1, 12, 1.15

(56) References Cited

U.S. PATENT DOCUMENTS

| | | | |
|---|---|---|---|
| 4,733,665 | * | 3/1988 | Palmaz .................. 623/1 X |
| 4,893,623 | * | 1/1990 | Rosenbluth ............ 606/192 |
| 5,071,407 | * | 12/1991 | Termin et al. ......... 606/194 X |
| 5,197,978 | * | 3/1993 | Hess ...................... 623/1 |
| 5,397,355 | * | 3/1995 | Marin et al. ........... 623/12 |
| 5,449,373 | * | 9/1995 | Pinchasik et al. ..... 606/198 |

FOREIGN PATENT DOCUMENTS

| | | |
|---|---|---|
| 0 566 807 A1 | 10/1993 | (EP). |
| 8902755 * | 9/1988 | (WO). |
| WO 95/09584 | 4/1995 | (WO). |

* cited by examiner

*Primary Examiner*—Michael H. Thaler

(57) ABSTRACT

With the foregoing in mind, the stent as described in this invention comprises a plurality of expandable cells. The cells are arranged circumferentially about the stent so that the stent in an unexpanded condition has a generally cylindrical construction and the expandable cells contain at least one metal bridge and at least one other circumferential arrangement of cells, and the bridge is initially arranged in a folded condition in the stent. When the cells expand, the bridge lengthens to a generally straight configuration. This straight configuration forms an arc of a circle about the cylindrical expandable stent. Ideally, there are multiple bridge connections made so that the stent has a full circumferential solid cross section along at least a portion of the cylindrical device.

4 Claims, 4 Drawing Sheets

RADIAL STRENGTH STENT

FIELD OF THE INVENTION

Generally this invention relates to stents for placement within lumens of the body. More specifically, this invention relates to providing strengthened stents for placement within blood vessels.

BACKGROUND OF THE INVENTION

The use of stents and materials for stents has gained popularity with the success of the Palmaz and Palmaz-Schatz stents marketed by Johnson & Johnson Interventional Systems, Warren, N.J. These stents are generally radially expandable cells and are well described in U.S. Pat. No. 4,733,655 to Palmaz incorporated herein by reference and the progeny of patents following the seminal Palmaz patent. Essentially, the stent comprises a material which is balloon expandable beyond its elastic limit. Generally these stents are formed from metal. This stent, when expanded beyond this elastic limit, maintains its position within the lumen of the body. The stent is able to hold open the lumen while maintaining its diameter beyond the elastic limit. This helps to enable passage of material through the lumen, most notably the flow of blood through the arteries, especially the coronary arteries.

It has been noted that in some instances one may desire to limit the amount of expansion of a balloon expandable stent. This may be (for instance) in situations where the lumen is of a known size and it is desired to have the stent be no more than the known size. While the manufacturer can certainly devise stents with the limitations of the known lumen in mind, in some instances it may be desirable to nevertheless limit the size of the stent so that the user can effectively choose a final diameter of the stent.

In addition, it has been found that it may be desirable to enhance circular or "hoop" strength while maintaining the stent beyond the elastic limit of the metal surface of the stent. This increased hoop strength may be useful in lumens where there are relatively high forces acting around the circumference of the stent. This may occur for instance in the arteries of the body.

With the foregoing in mind, the stent as described in this invention comprises a plurality of expandable cells. The cells are arranged circumferentially about the stent so that the stent in an unexpanded condition has a generally cylindrical construction and the expandable cells contain at least one metal bridge and at least one other circumferential arrangement of cells, and the bridge is initially arranged in a folded condition in the stent. When the cells expand, the bridge lengthens to a generally straight configuration. This straight configuration forms an arc of a circle about the cylindrical expandable stent. Ideally, there are multiple bridge connections made so that the stent has a full circumferential solid cross section along at least a portion of the cylindrical device.

The foregoing will be better understood in connection with drawings relating to the present invention.

DESCRIPTION OF THE DRAWINGS

FIG. 1 is a view of one cell, FIG. 2 is a view of expanded cells, and FIG. 3 is a perspective view of the cells arranged around the stent;

DETAILED DESCRIPTION OF THE INVENTION

Figure 1:
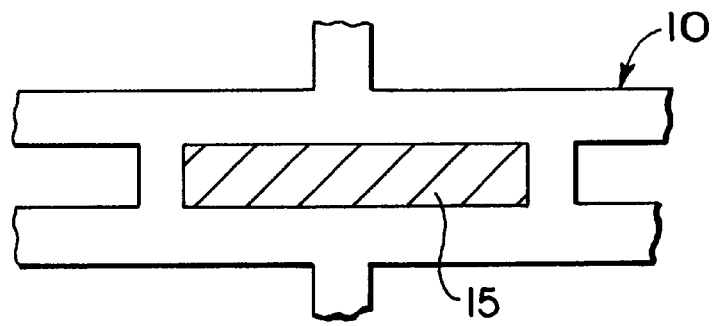
FIGS. 1, 2 and 3 are drawings of a prior art stent where
Figure 2:
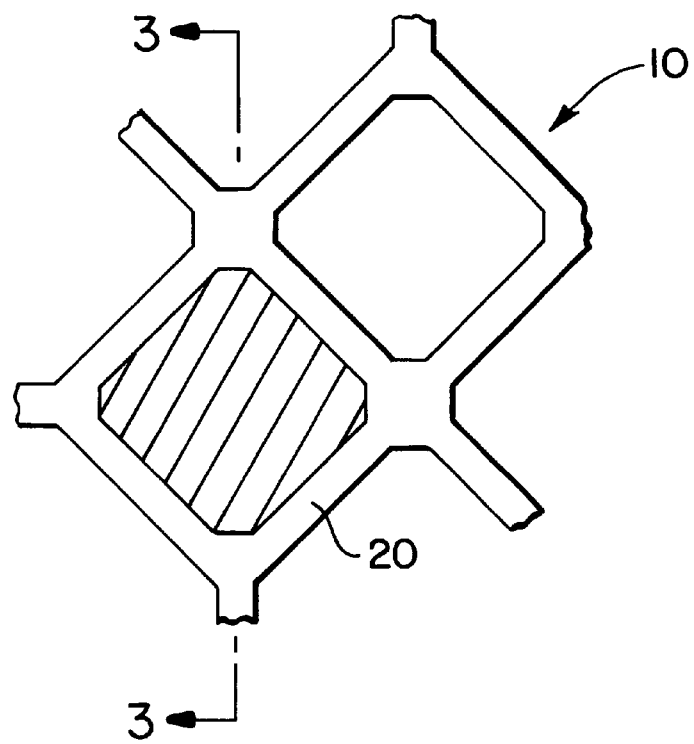
Figure 3:
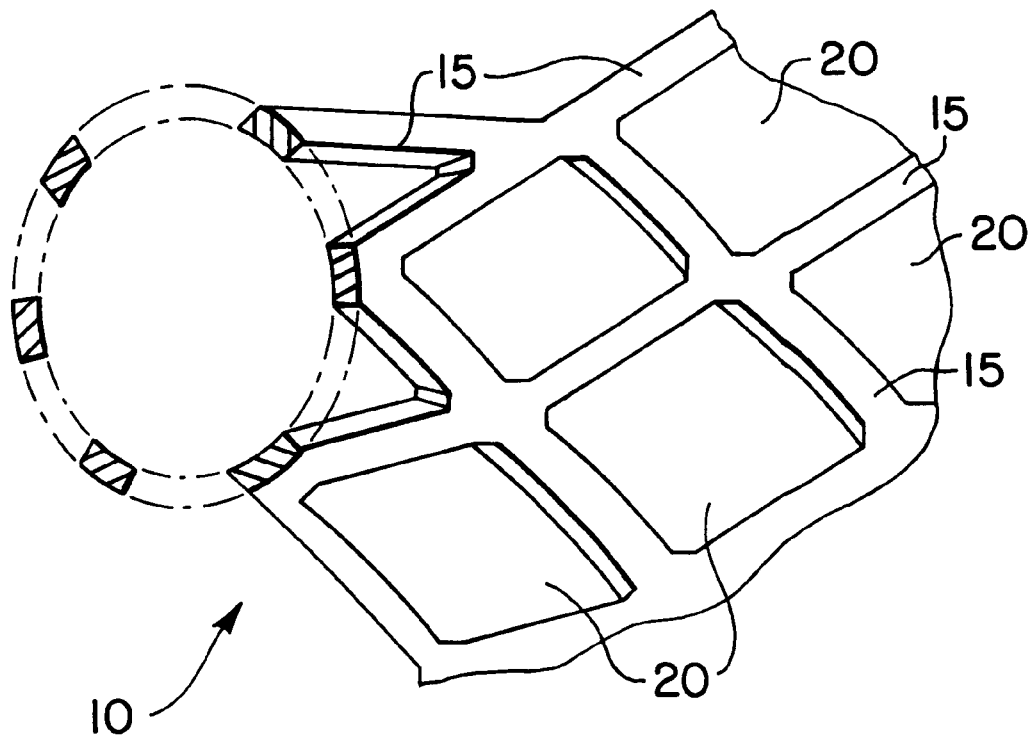

As seen in FIGS. 1, 2 and 3, a typical metallic balloon expandable stent 10 contains a number of expandable cells 20. These cells 20 are arranged circumferentially around the cylindrical stent 10. When in its unexpanded condition, the cells form a generally solid cylinder containing lengthwise slots 15 which allow for expansion. When expanded, these cells 20 are capable of expanding beyond their elastic limit. When this occurs, the cells take on a generally "diamond" shaped configuration. The plurality of diamonds are contained about the entire circumference of the cylinder.

When maintaining this configuration, however, as seen from FIG. 3, there is in theory, no limit placed ring on the size of the expanded cylinder. Thus, the user of the device arguably can expand the cells well beyond their elastic limit. There is not the requisite "hoop" strength that will maintain the cells in a limited geometric opening.

Figure 4:
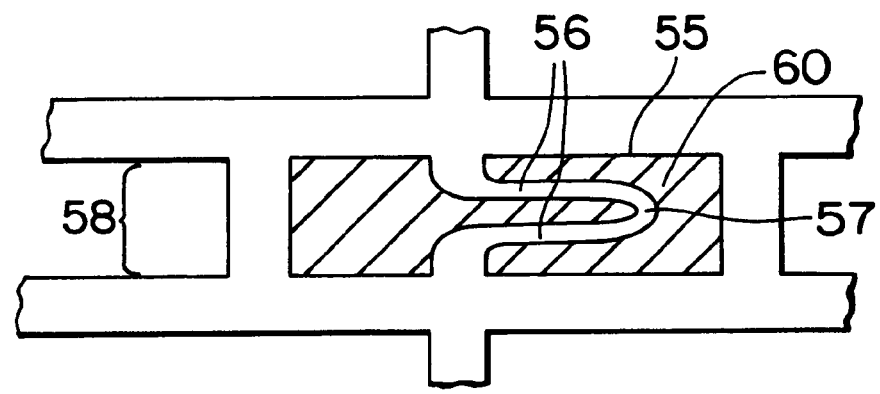
FIGS. 4, 5 and 6 are analogous drawings of a stent containing the improved invention.
Figure 5:
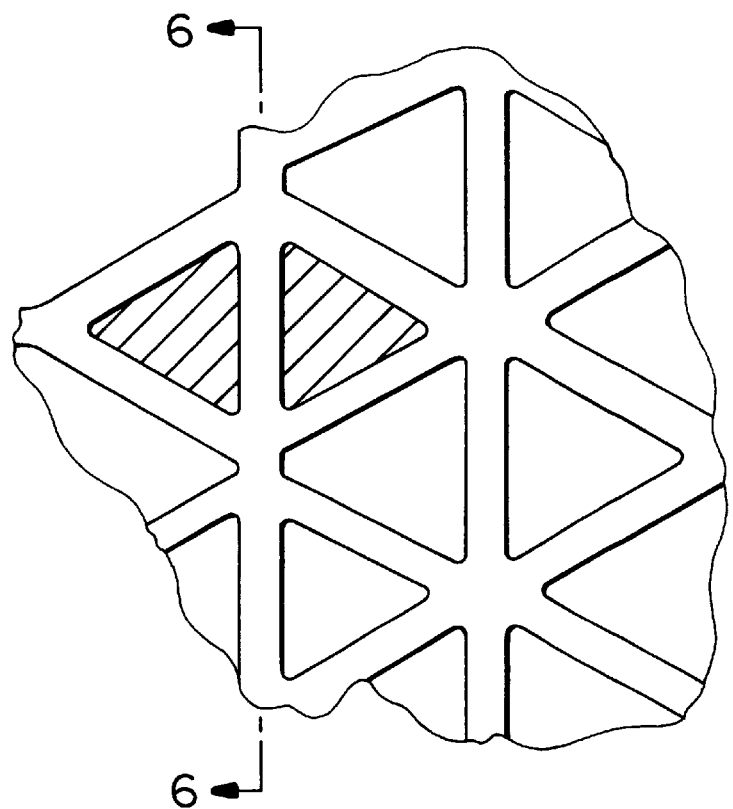
Figure 6:
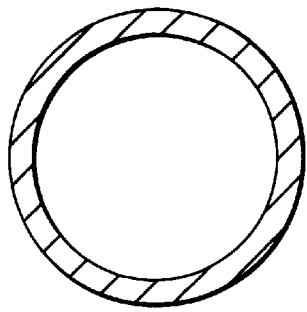
Figure 6A:
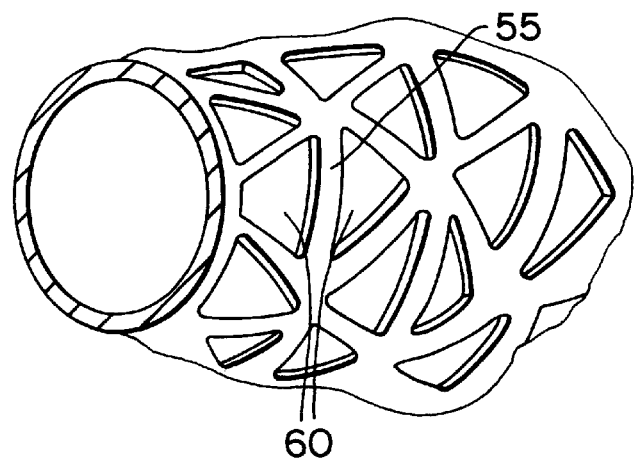

This is distinct from the device described in FIGS. 4–6. Therein, there are also contained a plurality of expandable cells 60. These cells are similarly arranged circumferentially around the stent 50. However, as seen from FIG. 4 and 5, there are contained cells 60 separated by "Z"-shaped" bridge sections 55 which are folded in their initial state about the generally cylindrical stent. The "Z"-shaped bridge may be oriented so that its legs 56 run either parallel or perpendicular to the axis of stent 50. The connecting leg 57 connects leg 56. When the stent 50 is expanded, these bridges 55 unfold within the slots 58 forming cells 60 so that now, the expanded bridges are arranged circumferentially about the cross section of the device. This forms a "ring" of metal in the expanded device. The characteristics of this "ring" of metal as seen in FIG. 6 are numerous. Because there is a ring of metal, it is much more difficult to expand the bridges circumferentially beyond its elastic limit. Thus, there is in general a limiting dimension of the expanded ring. This limiting dimension thereby creates a limiting dimension on the expanded stent, which may be desirable in certain instances.

Also, however, there is now with this ring of metal a stronger cross section of material. Again, it may be desirable to provide an enhanced strength in the circumferential direction. The continuous ring of metal allows for such enhanced circumferential strength.

Figure 7:
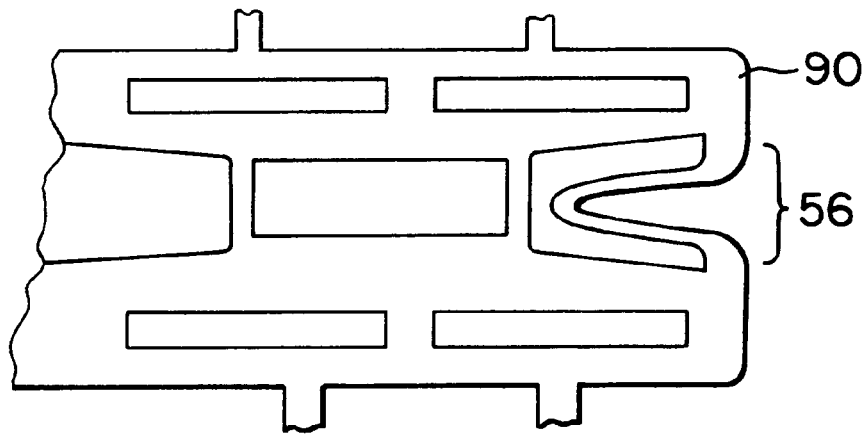
FIGS. 7 and 8 are drawings of a second potential embodiment of the stent of the present invention.
Figure 8:
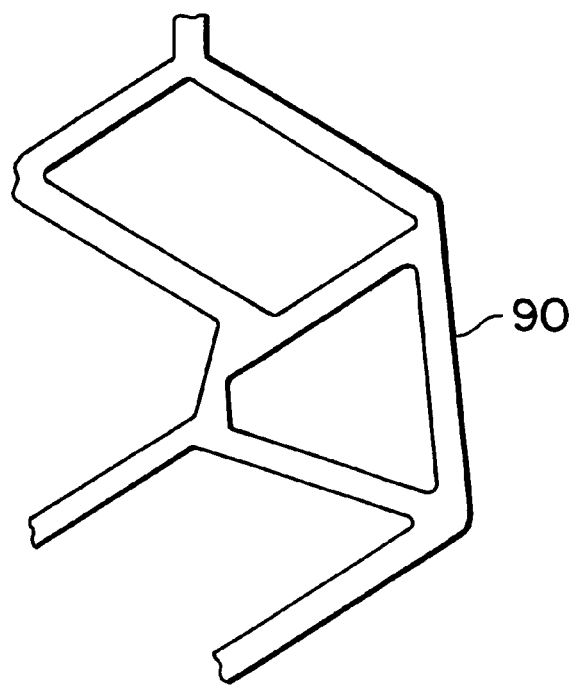

As seen in FIGS. 7 and 8, the bridge sections 56 may be contained at the end 90 of the stent 50, to form a ring of metal at the end of the stent 50.

Thus, the device described herein is a mechanism which allows for an enhanced strength performance, as well as enhanced dimensional opening in a standard balloon expandable stent. Therefore, the invention associated with this device is to be derived the following claims and their equivalents.

What is claimed is:

1. A stent comprising:
   a plurality of expandable cells, said cells arranged circumferentially about said stent so that said stent when in an unexpanded condition has a generally cylindrical construction; and
   at least one of said expandable cells containing a metal bridge therein, said bridge initially arranged in a folded condition in said; and wherein when said cells expand, said bridge lengthens to a generally straight configuration, such that said straightened bridge forms an arc of a circle about said expanded cylindrical stent.

2. The stent of claim 1 wherein there are a plurality of bridges arranged circumferentially in said stent, and said straightened bridges forming a continuous ring around said stent cylinder.

3. The stent of claim 2 wherein said straightened bridges forming said continuous ring are located at an longitudinal end of said stent cylinder.

4. A stent comprising:

a plurality of expandable cells, said cells arranged circumferentially about said stent so that said stent when in an unexpanded condition has a generally cylindrical construction; and at least one of said expandable cells containing a metal bridge therein, said bridge initially arranged in a folded condition in said cell; and wherein when said cells expand, said bridge lengthens to a generally straight configuration, such that said straightened bridge forms an arc of a circle about said expanded cylindrical stent; and wherein there are a plurality of bridges arranged circumferentially in said stent, and said straightened bridges forming a continuous ring around said stent cylinder.

* * * * *